(12) United States Patent
Kube, II

(10) Patent No.: US 8,679,184 B2
(45) Date of Patent: Mar. 25, 2014

(54) INTERBODY CAGE FOR SPINAL FUSION AND METHOD OF IMPLANTING INTERBODY CAGES INTO SPINES

(75) Inventor: Richard A. Kube, II, Peoria, IL (US)

(73) Assignee: 5K IP-1 LLC, Reno, NV (US)

( * ) Notice: Subject to any disclaimer, the term of this patent is extended or adjusted under 35 U.S.C. 154(b) by 1 day.

(21) Appl. No.: 13/441,471

(22) Filed: Apr. 6, 2012

(65) Prior Publication Data
US 2013/0096683 A1    Apr. 18, 2013

Related U.S. Application Data

(60) Provisional application No. 61/473,126, filed on Apr. 7, 2011.

(51) Int. Cl.
*A61F 2/44*         (2006.01)
(52) U.S. Cl.
USPC ........................................ 623/17.16
(58) Field of Classification Search
CPC .................................. A61F 2/44; A61B 17/70
USPC ........... 606/246–249, 279, 86 A, 90, 99, 100, 606/105; 623/17.11, 17.16
See application file for complete search history.

(56) References Cited

U.S. PATENT DOCUMENTS

| | | | |
|---|---|---|---|
| 4,878,915 | A | 11/1989 | Brantigan |
| 5,306,309 | A | 4/1994 | Wagner et al. |
| 5,431,658 | A * | 7/1995 | Moskovich ..................... 606/99 |
| 5,443,514 | A | 8/1995 | Steffee |
| 6,176,882 | B1 | 1/2001 | Biedermann et al. |
| 6,290,724 | B1 | 9/2001 | Marino |
| 6,375,655 | B1 | 4/2002 | Zdeblick et al. |
| 6,666,891 | B2 | 12/2003 | Boehm, Jr. et al. |
| 6,719,794 | B2 | 4/2004 | Gerber et al. |
| 7,226,483 | B2 | 6/2007 | Gerber et al. |
| 7,655,010 | B2 | 2/2010 | Serhan et al. |
| 2005/0075734 | A1 * | 4/2005 | Fulton et al. ............... 623/17.16 |
| 2006/0106462 | A1 | 5/2006 | Tsou |
| 2008/0177275 | A1 | 7/2008 | Wing et al. |
| 2008/0269764 | A1 | 10/2008 | Blain et al. |
| 2009/0030422 | A1 | 1/2009 | Parsons et al. |

(Continued)

OTHER PUBLICATIONS

Cedars-Sinai, Transforminal Lumbar Interbody Fusion (TLIF), 2010, 1 page, internet publication obtained from www.cedars-sinai.edu.

(Continued)

*Primary Examiner* — Pedro Philogene
*Assistant Examiner* — David Comstock
(74) *Attorney, Agent, or Firm* — Thompson Coburn LLP

(57) ABSTRACT

A spinal interbody fusion implant has an impact rod fitting that is configured and adapted to be connected to an impact rod during implantation of the implant. The implant also comprises one or more openings that are encircled by portions of the implant and that extend into the top of the implant and continue through to and out of the bottom of the implant. The top and bottom of the implant each have a load bearing footprint. Each of the load bearing footprints has a centroid that is closer to the leading end of the implant than to the trailing end of the implant. A method of implanting a spinal interbody fusion implant between two vertebrae of a spine comprises inserting the implant into a patient through a posterior incision and guiding the implant into a position between the two vertebrae using a pair of shims.

6 Claims, 10 Drawing Sheets

(56) References Cited

U.S. PATENT DOCUMENTS

| | | |
|---|---|---|
| 2009/0093883 A1 | 4/2009 | Carrasco |
| 2009/0177285 A1 | 7/2009 | Frey et al. |
| 2010/0152853 A1 | 6/2010 | Kirschman |
| 2010/0222784 A1 | 9/2010 | Schwab et al. |

OTHER PUBLICATIONS

Elite Surgical Supplies (Pty) Ltd., Elite TLIF—Spinal Cage System and Vertifix—Pedicle Screw System, obtained Dec. 14, 2010 from auckland.co.za.elite.htm, 5 pages.

Spine Smith, Products: Hardware Technologies, 2010, 6 pages, internet publication obtained from www.spinesmithusa.com.

Elite Surgical Supplies (Pty) Ltd., TLIF Cages, obtained Dec. 14, 2010 from www.elitesurgical.com, 2 pages.

Dykes et al., Unilateral Lumbar Interbody Fusion Technique, Syryker Spine publication for AVS UniLIF Peek spacer System: UniLIF Surgical Technique, 2010, 24 pages.

\* cited by examiner

INTERBODY CAGE FOR SPINAL FUSION AND METHOD OF IMPLANTING INTERBODY CAGES INTO SPINES

CROSS-REFERENCE TO RELATED APPLICATIONS

This patent application is a non-provisional of provisional patent application Ser. No. 61/473,126, which was filed on Apr. 7, 2011.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

This invention pertains to methods and devices for spinal stabilization, repair, and/or reconstruction. More particularly, this invention pertains to devices and methods for minimally invasive or open techniques for interbody fusion, for example, of the lumbar spine. Embodiments of the invention are applicable to transforaminal lumbar interbody fusion ("TLIF") and/or transforaminal posterior lumbar interbody fusion ("TPLIF").

2. General Background

Traditional devices and methods for lumbar interbody fusion often do not use minimally invasive techniques and often do not provide adequate surface area to adequately stabilize the spine. Traditional TLIF and TPLIF methods utilizing lumbar interbody fusion implants and unilateral screws often utilize implants that have footprints (i.e., projected horizontal bearing surface area capable of bearing vertical compression loads) that are inadequate to properly stabilize an anterior spine. Such implants often lead to subsidence, may provide insufficient rigidity and interbody fusion, and often require stripping of the muscles in and around the spine. As such, the inventor has appreciated that there is a need for an apparatus and method for minimally invasive lumbar interbody fusion that provides sufficient rigidity and that does not lead to subsidence.

SUMMARY OF THE INVENTION

In one aspect of the invention, a spinal interbody fusion implant in accordance with the invention comprises a leading end, a trailing end, opposite sides, a top, and a bottom. The trailing end has an impact rod fitting that is configured and adapted to be connected to an impact rod during implantation of the implant. The implant also comprises one or more openings that are encircled by portions of the implant and that extend into the top of the implant and continue through to and out of the bottom of the implant. The top and bottom of the implant each have a load bearing footprint. Each of the load bearing footprints has a centroid that is closer to the leading end of the implant than to the trailing end of the implant. The opposite sides and the leading and trailing ends of the implant each have a maximum horizontal dimension. The horizontal dimensions of the sides of the implant are greater than the horizontal dimensions of the leading and trailing ends of the implant.

In another aspect of the invention, a method of implanting a spinal interbody fusion implant between two vertebrae of a spine in accordance with the invention comprises inserting the implant into a patient through a posterior incision and guiding the implant into a position between the two vertebrae using a pair of shims. The implant is between the shims and the shims are between the vertebrae as the implant is guided into place.

Further features and advantages of the present invention, as well as the operation of the invention, are described in detail below with reference to the accompanying drawings.

DETAILED DESCRIPTION

Figure 1:
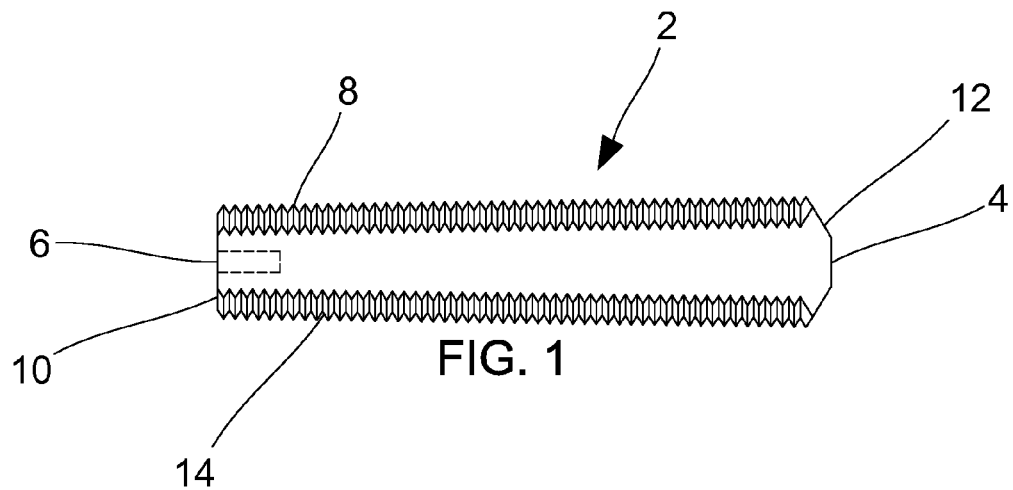
FIG. 1 depicts the medial side view of an embodiment of an interbody fusion implant in accordance with the invention.

Reference numerals in the written specification and in the drawing figures indicate corresponding items.

For purposes of describing the invention, the top of an implant herein means the portion of the implant that is generally superior in position relative to the remainder of the implant after the implant has been positioned between two vertebrae of a spine and when the spine is in a normal upright position. Similarly, the bottom of an implant means the portion of the implant that is generally inferior in position relative to the remainder of the implant when the implant has been positioned between the two vertebrae and the spine is in a generally upright position.

Figure 2:
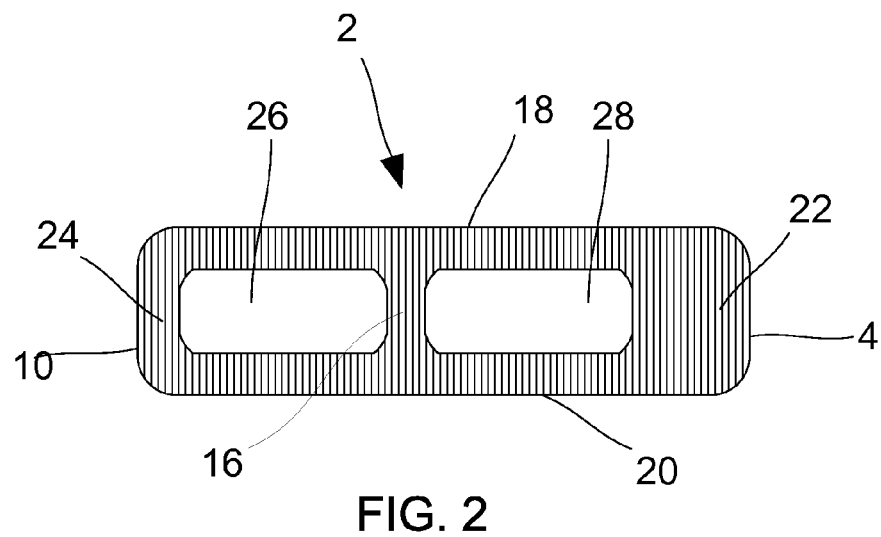
FIG. 2 depicts the top view of the implant shown in FIG. 1, the bottom view being identical thereto.
Figure 3:
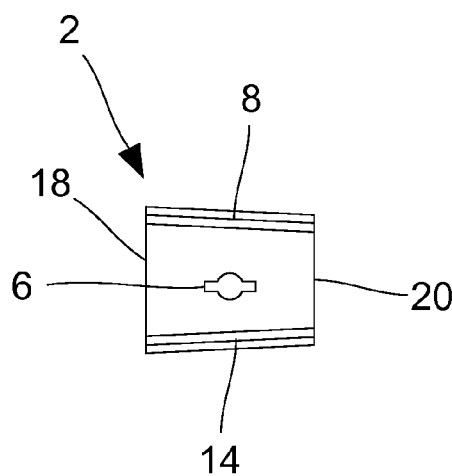
FIG. 3 depicts the trailing end of the implant shown in FIGS. 1 and 2.
Figure 4:
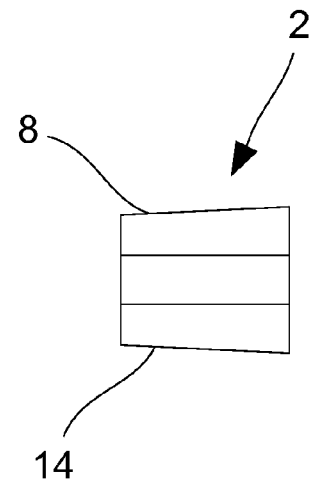
FIG. 4 depicts the leading end of the implant shown in FIGS. 1-3.

Some embodiments of spinal interbody fusion implants 2 in accordance with the invention are depicted in FIGS. 1-4 and 9-11. Each implant 2 may serve as an interbody spacer, disc replacement, or vertebral body replacement, that is positionable between an upper vertebral body 38 and a lower vertebral body 40 (See FIGS. 5-8). Referring to FIGS. 1, 3, and 4, each implant includes a top surface 8 and a bottom surface 14 that are configured to engage an inferior endplate of upper vertebral body 38 and a superior endplate of lower vertebral body 40 (See FIG. 6). The total projected contact surface of the top surface 8 and the bottom surface 14 may be referred to herein as a "footprint".

Figure 5:
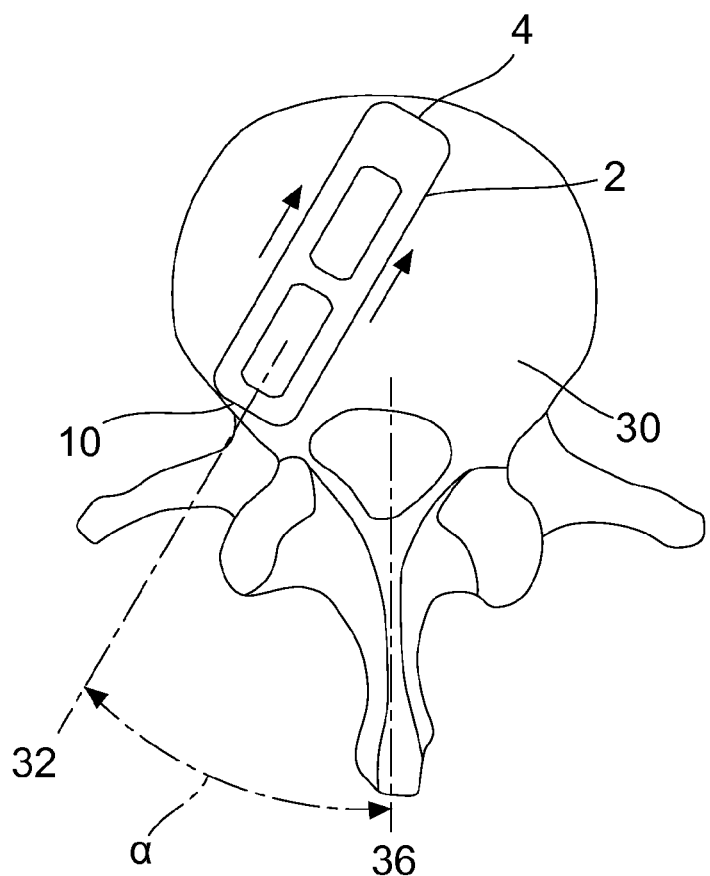
FIG. 5 depicts a horizontal cross-section of a spine and the implant shown in FIGS. 1-4 positioned in the spine at an implantation angle $\alpha$.
Figure 6:
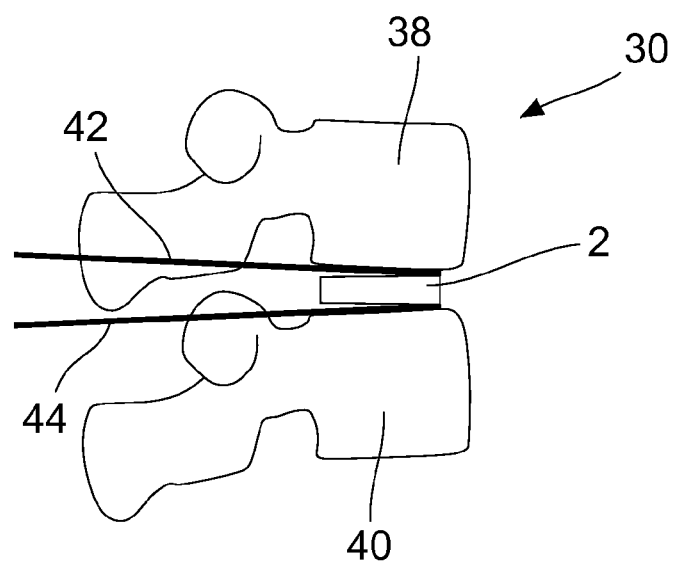
FIG. 6 depicts a lateral view of a spine and the insertion of the implant shown in FIGS. 1-4 using the shims describe herein.
Figures 7, 8:
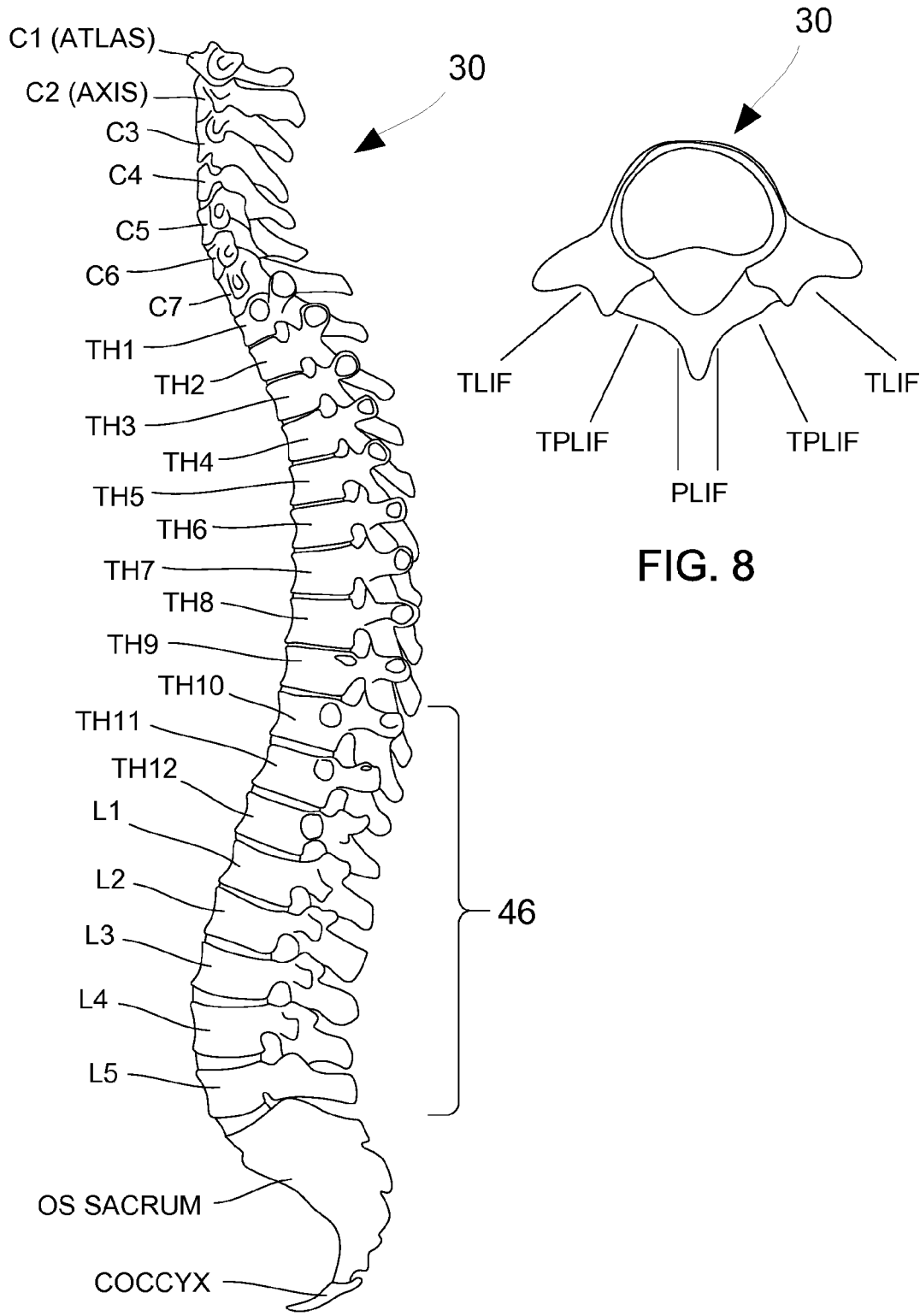
FIG. 7 depicts a typical spine of a human body.
FIG. 8 depicts various implantation angles for implanting the implant shown in FIGS. 1-4 into a spine.

Referring to FIGS. 5, 6, and 8, the implants 2 may be used for any spinal fusion procedure at any implantation vector 32, implantation angle 34, or location about the spine 30. The implants may be used for TLIF and/or TPLIF procedures (See FIGS. 5, 6, and 8). With reference to FIG. 7, the implants 2 may be positioned in the lower spinal region 46, which includes any interbody space at or near the lumbar region (L1 through sacrum) or the lower thoracic region (TH10 through L1). The implants 2 may be positionable in or near an anterior subchondral region of an anterior ring of a vertebral body. The implants 2 may be solid, rigid, and/or support significant spinal loads. The implants 2 may be positionable near denser bone to reduce subsidence and/or sinking into bone.

The implants 2 may comprise metal, such as titanium, stainless steel, tantalum, cobalt-chrome, any other biocompatible metal, or any combination thereof. The implants may also or alternatively comprise polymeric material, such as polyetherketone (PEK), polyetheretherketone (PEEK), polyetherketoneketone (PEKK), polyaryletherketone (PAEK), or any combination thereof. Any portion or all of the implant 2 may include any metal, polymer, any other biocompatible material, or any combination thereof, which may be a different material than the material used in another portion of implant.

Referring to FIGS. 1, 2, 4, 9, and 11, each implant 2 comprises a leading end 4. The leading end 4 is positionable at the anterior spine, for example, at the anterior subchondral ring of the spine and/or at the anterior portion of a vertebral body disc space of the spine.

Each implant 2 may be any size or dimension suitable for spinal fusion procedures. That being said, the dimensions provided herein are intended to serve as examples and should not limit the dimensions of the implants claimed herein. Preferably, the maximum distance from one side surface 18 of each implant 2 to the opposite side surface 20 thereof (referred to herein as the "width") is in the range of 10 to 30 millimeters ("mm"), and more preferably is in the range of 14 to 20 mm. Preferably, the maximum distance from the top surface 8 to the bottom surface 14 (referred to herein as the "height") is in the range of 2 mm to 16 mm, and more preferably is in the range of 8 to 14 mm. Preferably the maximum distance from the leading end 4 to the trailing end 10 (referred to herein as "length") is in the range of 20 mm to 60 mm. Preferably, the implants are formed in numerous sizes, in various increments of 2 mm in height and width and 5 mm increments of length.

Referring to FIGS. 2 and 5, each implant 2 preferably includes one or more openings 26, 28. The openings 26, 28 preferably extend vertically through the implant 2 such that they are configured and adapted for accepting bone graft material to eventually fuse the vertebrae between which the implant is placed. The openings 26, 28 are preferably separated by a crossbar 16. Bone graft material may be positioned in an opening 26, 28 that will lie at or near a portion of the spine where the bone quality is suitable for spinal fusion.

With further reference to FIG. 2, the distance from leading end 4 of each implant 2 to the nearest opening 28 is preferably in the range of 6 to 10 mm, more preferably 6 mm in an implant with a length from 25 to 30 mm, 8 mm in an implant with a length from 35 to 50 mm, and 10 mm in an implant with a length exceeding 50 mm. Thus, this leading portion 22 of each implant has a relatively large bearing footprint (i.e., projected horizontal bearing surface area capable of bearing vertical compression loads) as compared to the remainder of the implant. Referring to FIG. 2, this leading portion 22 of the implant 2 is configured to enhance contact surface area, improve load sharing characteristics, and provide greater stability of the implant 2. In comparison, the distance from the either opposite side surface 18, 20 to the opening or openings 26, 28 therebetween is preferably about 2 to 3 mm. Similarly, the distance from trailing end 10 to the nearest opening 26 (across area 24 shown in FIG. 2) is about 2 to 3 mm, as is the distance between the openings 26, 28.

The implants 2 may also include surface features such as, but not limited to, serrations, chamfers, rounds, slots, screw holes, porous coating, and/or radiopaque markers. As shown in FIGS. 1, 3, and 4, the implants 2 may also have top 8 and bottom 14 surfaces that provide the implant with an oblique lordotic shape of between zero and ten degrees, and more preferably of about 5 degrees. For example, the oblique lordotic may include at least one or two surfaces that taper at an angle that is offset from the longitudinal and transverse axes of the implant 2. The height of the implant 2 may increase from the trailing end 10 to leading end 4 (as shown in FIG. 1) and/or decrease from one side surface 18 to the other side surface 20 (as shown in FIG. 3). Alternatively, the oblique lordotic shape of the implant may be opposite to that shown in FIGS. 1 and 3. For example, the height may decrease from the trailing end 10 to the leading end 4 and the implant 2 could be inverted, thereby flipping the side-to-side slope direction.

Figure 9:
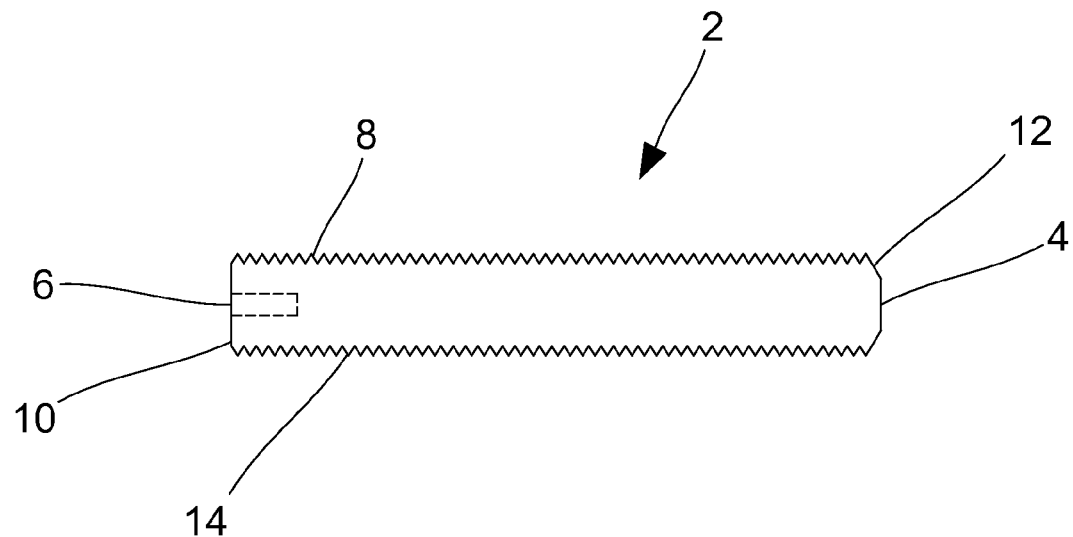
FIG. 9 depicts the medial side view of an alternate embodiment of an interbody fusion implant in accordance with the invention.
Figure 10:
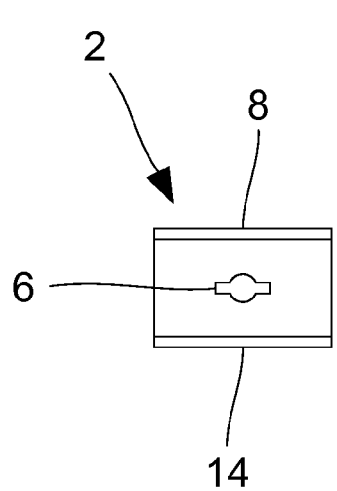
FIG. 10 depicts the trailing end view of the implant shown in FIG. 9.
Figure 11:
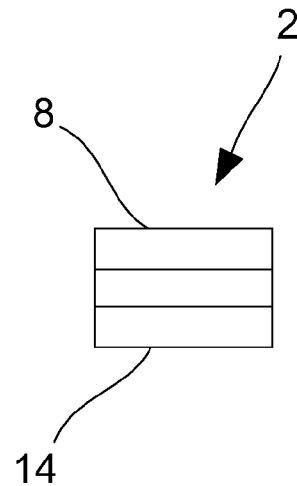
FIG. 11 depicts the leading end view of the implant shown in FIGS. 9 and 10.
Figure 12:
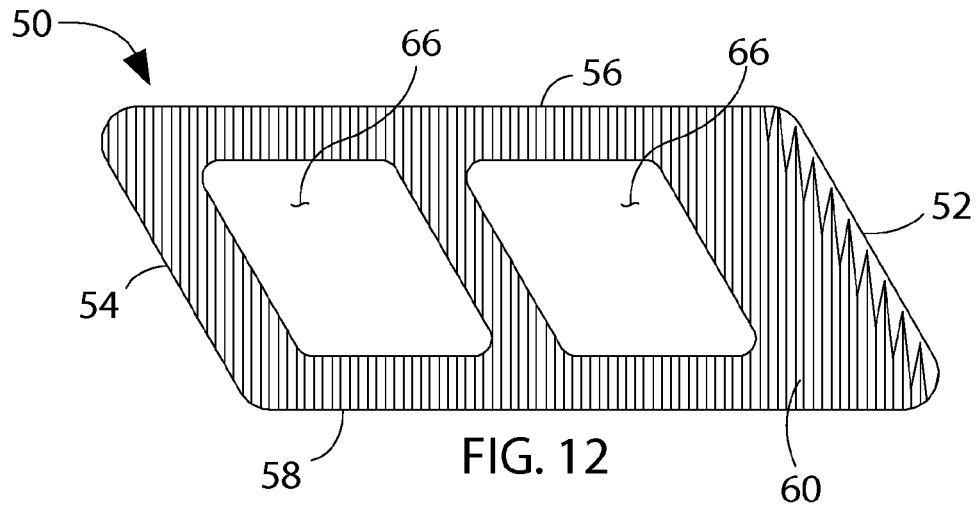
FIG. 12 depicts a top view of another embodiment of an implant in accordance with the invention, which has leading and trailing ends that are skewed relative to its sides.
Figure 13:
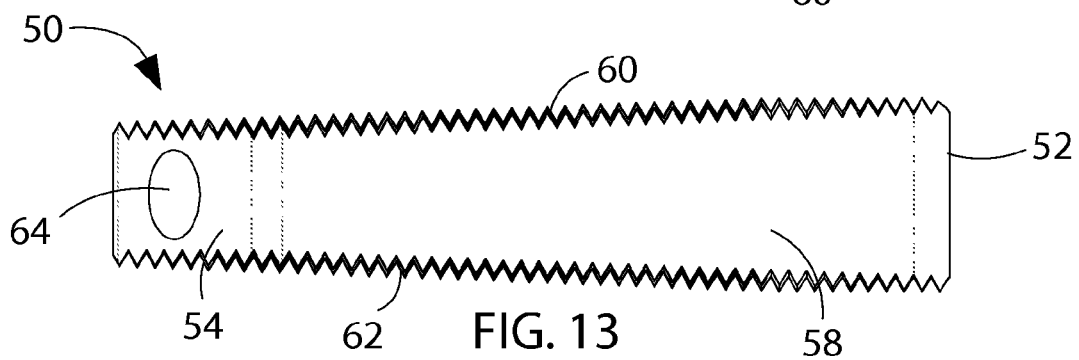
FIG. 13 depicts the medial side view of the implant shown in FIG. 12.
Figure 14:
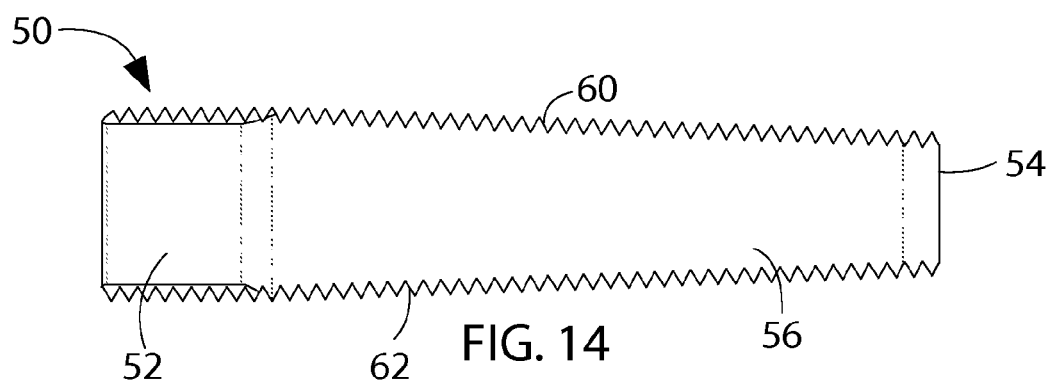
FIG. 14 depicts the lateral side view of the implant shown in FIGS. 12 and 13.
Figures 15, 16:
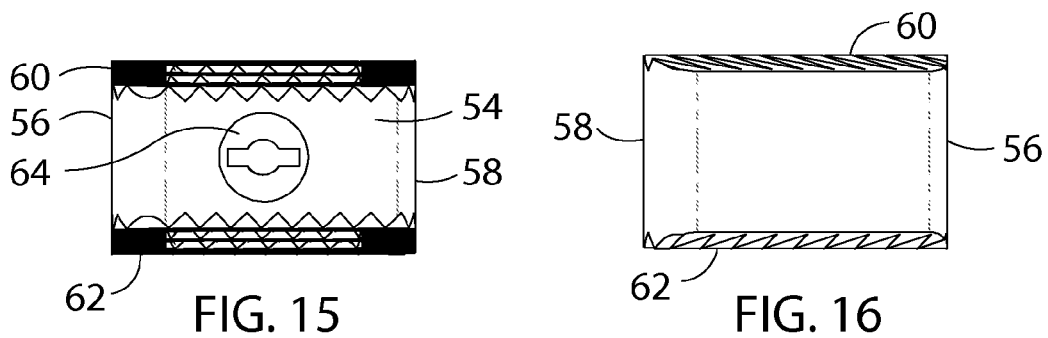
FIG. 15 depicts the trailing end view of the implant shown in FIGS. 12-14.
FIG. 16 depicts the leading end view of the implant shown in FIGS. 12-15.
Figure 17:
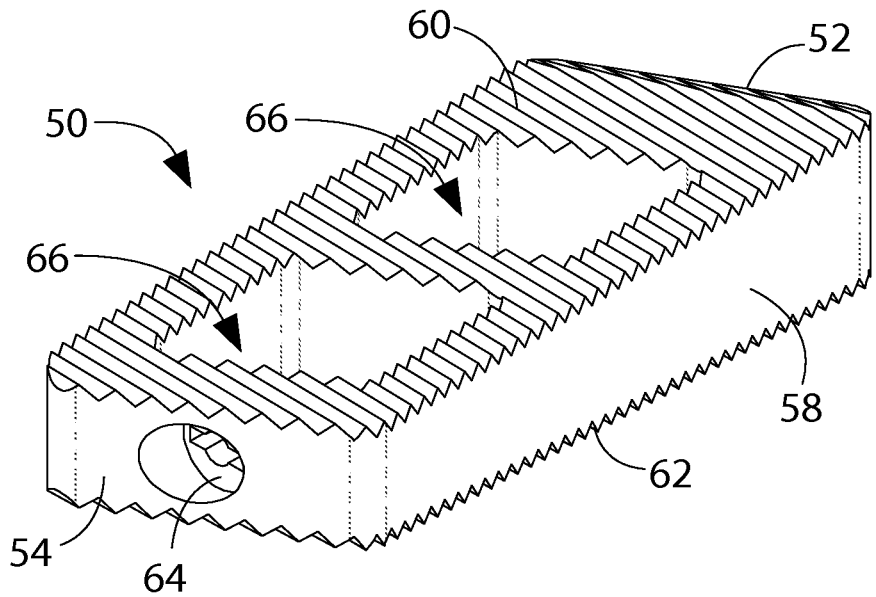
FIG. 17 depicts a perspective view of the implant shown in FIG. 12-16 and shows the trailing end, medial side, and top of the implant.
Figure 18:
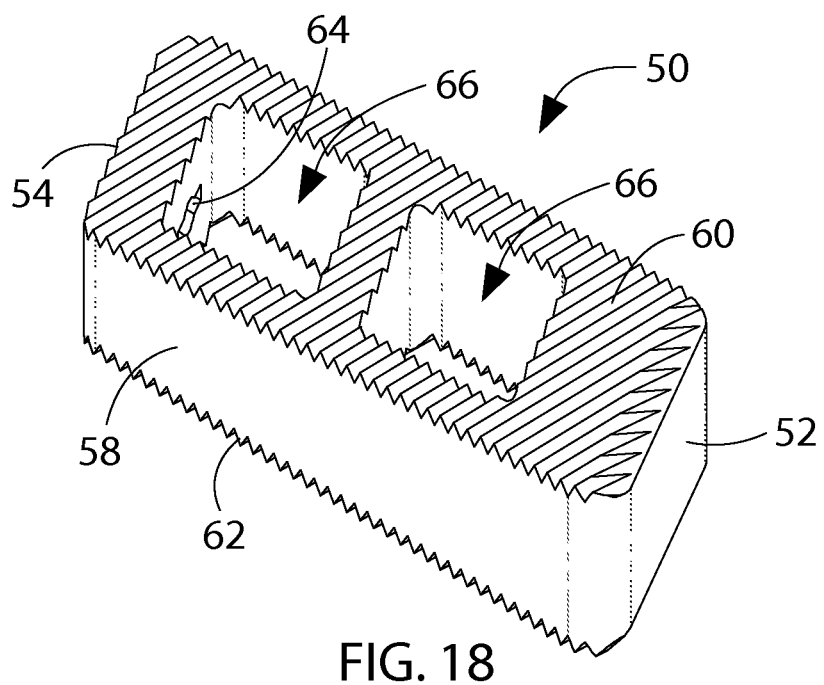
FIG. 18 depicts a perspective view of the implant shown in FIG. 12-17 and shows the leading end, medial side, and top of the implant.

Referring to FIGS. 1 and 9, the implants preferably include chamfers 12, which may assist in the implantation and/or advancement of implants. The chamfers 12 are preferably 0.1 to 10 mm chamfers, and more preferably are 1 mm chamfers positioned on top and bottom edges of the leading end of the implants. The trailing end preferably comprises an impact rod fitting 6 that is configured to be releasably attachable to an impact rod during implantation of the implant 2. Polymeric implants preferably comprise radiopaque markers.

Referring to FIG. 6, shims 42, 44 may be used to position the implants 2 into the disc space between vertebrae and/or to help protect the nerve roots and/or endplates of the vertebrae during the implantation of the implants. The shims 42, 44 may include blunt, curved, and/or flat surfaces. The shims 42, 44 may be formed of rigid, flexible, or shape memory material. The shims 42, 44 are preferably positioned in the disc space in a manner such that they guide the implant into the disc space during the impaction or pushing of the implants 2. The shims 42, 44 may force apart vertebrae to allow for placement of appropriate height implant 2 and/or to provide a layer of protection between nerve roots and boney end plates. After the implant 2 has passed into the disc space via the shims 42, 44, the implant 2 can be impacted and/or reoriented. After the implant 2 is positioned between the vertebrae, the shims 42, 44 can be removed. As a dimensional example, the shims 42 and 44 preferably have a width of 5-15 mm and a thickness 0.1 to 2 mm, and more preferably are 10 mm wide and 0.5 mm thick.

With reference to FIGS. 5, 7, and 8, procedures in accordance with the invention include TLIF and/or TPLIF procedures. Such procedures may utilize an implantation vector 32 having an implantation angle α of about 30 degrees from the midsagittal plane and an access path from posterolateral to anterolateral. The implants 2 may be inserted unilaterally, between the spinal muscles, and/or without cutting and/or substantially disrupting muscles of or near the midline of the spine. The procedures may provide direct access to the disc space for the implant 2 and/or allow for passage of the implant through an annulus of a spine. After a dissection is performed, the disc material in the interbody space may be removed and the endplates prepared for bone graft material. After the implant 2 is properly positioned, the disc space and/or the implant 2 may be packed with bone graft materials.

The implants 2 may be implanted using the Wiltse technique, which may include a paramedian incision utilizing the plane between a longissimus muscle and a multifidus muscle posteriorly to provide access toward a facet of a spine. The implants 2 may be implanted via the same as or similar approach as a lateral disc excision. The implants 2 may be implanted via cutting a portion of a superior articular process of a vertebral body below and/or gaining access into a disc lateral from center. Still further, the implants 2 may be implanted via cutting a portion of an inferior articular process of the vertebral body above.

The implants 2 may be implanted unilaterally or bilaterally using standard pedicle screw instrumentation. Given the larger footprint and contact surface area, especially adjacent the leading end of the implants 2, and implantation vector, the implants may provide more than sufficient stability for a unilateral technique. Thus, the cost for an additional implant or additional screws can be avoided. Likewise, using a unilateral technique in accordance with the invention, less tissue dissection is required and hence fusion procedures using the invention are less invasive, less traumatic to soft tissue, result in less blood loss, and theoretically yield faster healing and recovery times by limiting the collateral damage of surgery.

Another implant in accordance with the invention is shown in FIGS. 12-18. This implant 50 comprises many of the features of the implant 2 described above and the description of the implants described above generally applies to this alternative embodiment of an implant. The alternative implant 50 differs from the previously described implants in that its leading end 52 and trailing end 54 are skewed relative to its opposite sides 56, 58. Preferably the leading end 52 and trailing end 54 are skewed equally in a manner such the implant is rhomboidal in shape. The side 58 of the implant 50 that meets the leading end 52 at an acute angle is configured to be positioned medially after implantation. The side 56 of the implant 50 that meets the leading end 52 at an obtuse angle is configured to be positioned laterally after implantation. Preferably the top 60 and bottom 62 of the implant taper toward each other as the implant 50 extends from its leading end 52 to its trailing end 54, preferably at a five degree angle relative to each other. The slope of the taper preferably runs perpendicular to the leading 52 and trailing 54 ends of the implant 50 such that the top and bottom edges of the leading end 52 are parallel to each other, as are the top and bottom edges of the trailing end 54. Like with the other implant embodiments of the invention, this alternative implant 50 also comprises an impact rod fitting 64 formed in its trailing end 54, and has bone graft openings 66, each of which extends through the top and bottom of the implant and is encircled by the implant.

Figure 19:
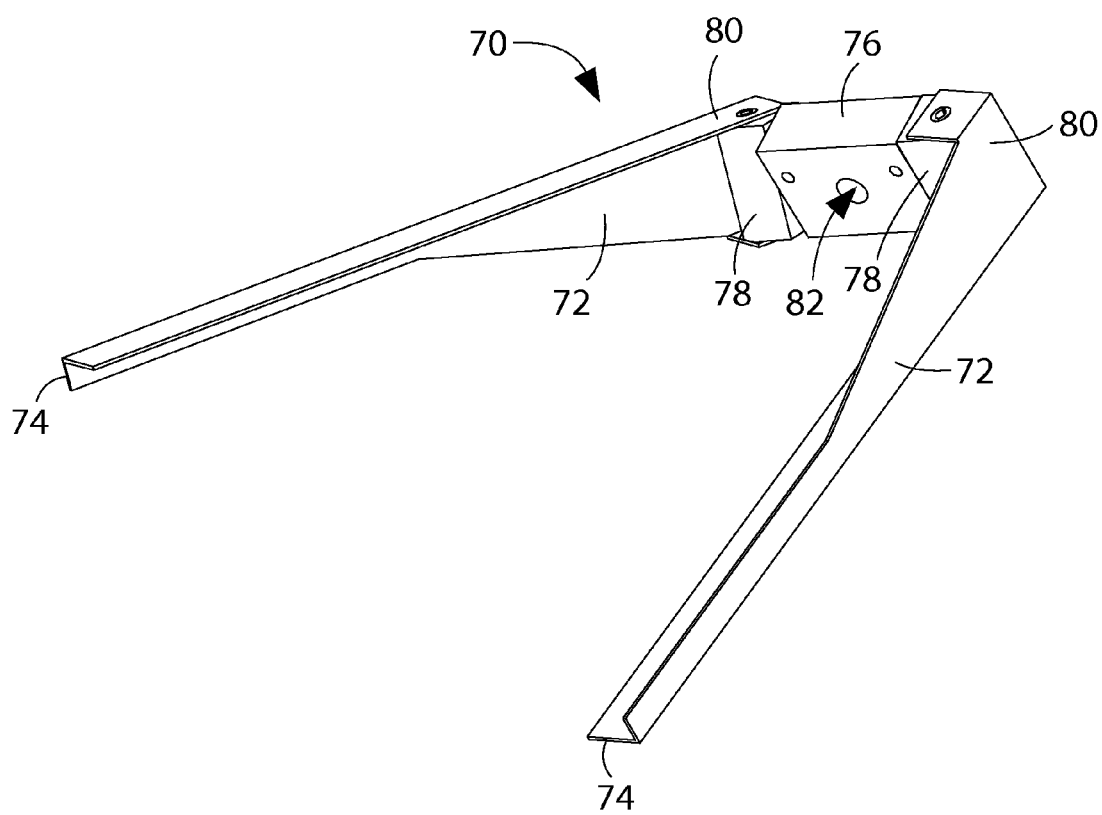
FIG. 19 depicts a shim tool in accordance with the invention.

A shim tool assembly 70 in accordance with the invention is shown in FIG. 19. The shim tool assembly comprises a pair of elongate shims 72. The distal end 74 and much of the remainder of each shim 72 preferably has an L-shaped cross-section. The L-shaped cross-section at the distal end 74 of each shim 72 preferably is approximately 10 mm wide and 5 mm high. The shim tool assembly also comprises a connecting member 76 and a pair of intermediate pivot members 78. The proximal end 80 of each shim 72 is pivotally connected to a respective one of the pivot members 78 about an axis. Likewise, each pivot member 78 is pivotally connected to the connecting member 76 about an axis that is perpendicular to the axis about which the respective shim 72 is attached to the pivot member. Thus each shim 72 is pivotally connected to the connecting member 76 with two degrees of pivotal freedom. The connecting member 76 comprises an impact rod guide hole 82 that extends through the connecting member perpendicular to axes about which the pivot members 78 are attached to the connecting member.

Figure 20:
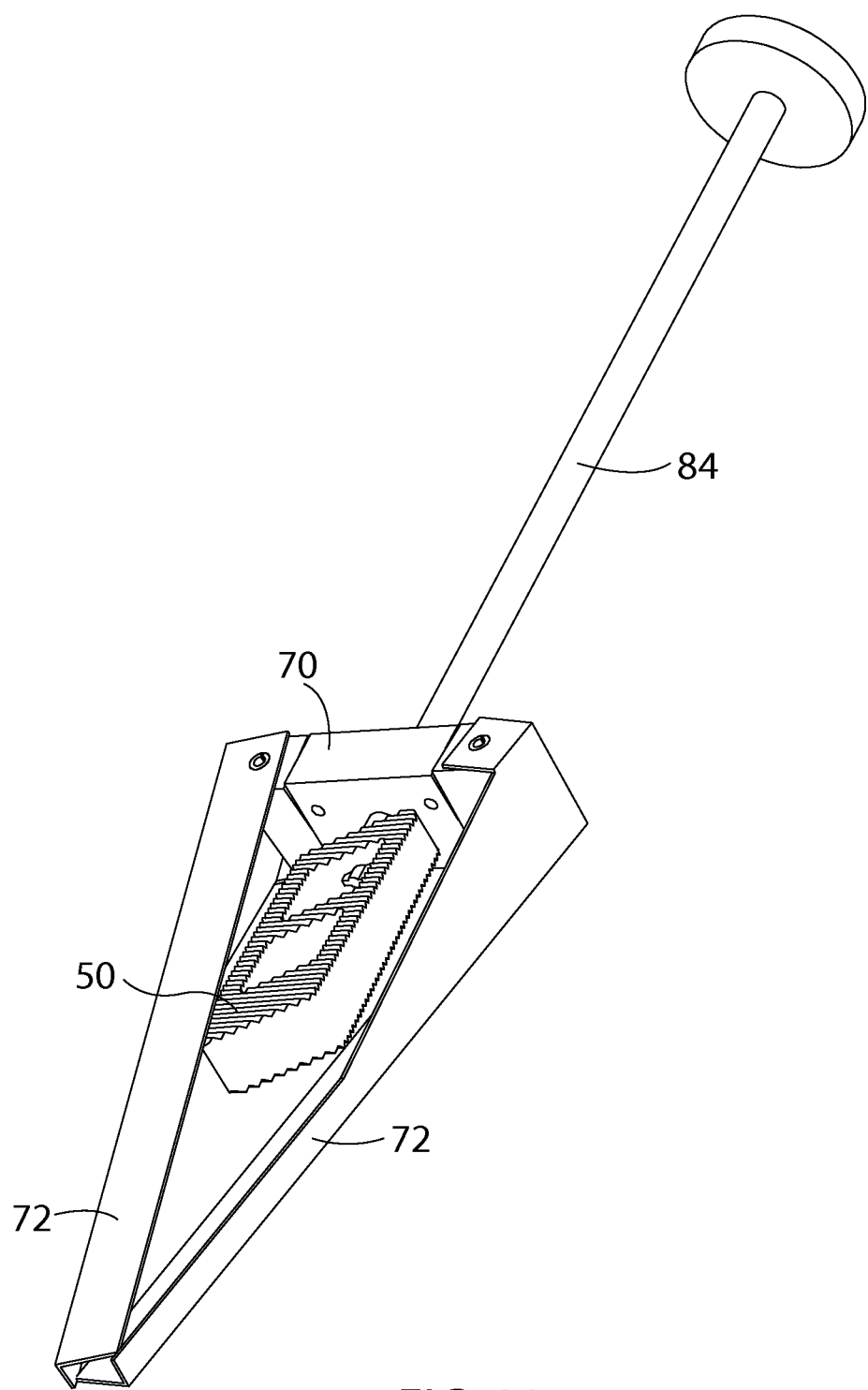
FIG. 20 depicts the shim tool shown in FIG. 19 with an implant and impact rod attached thereto, showing the shim tool in the configuration it is initially in during an implantation procedure.
Figure 21:
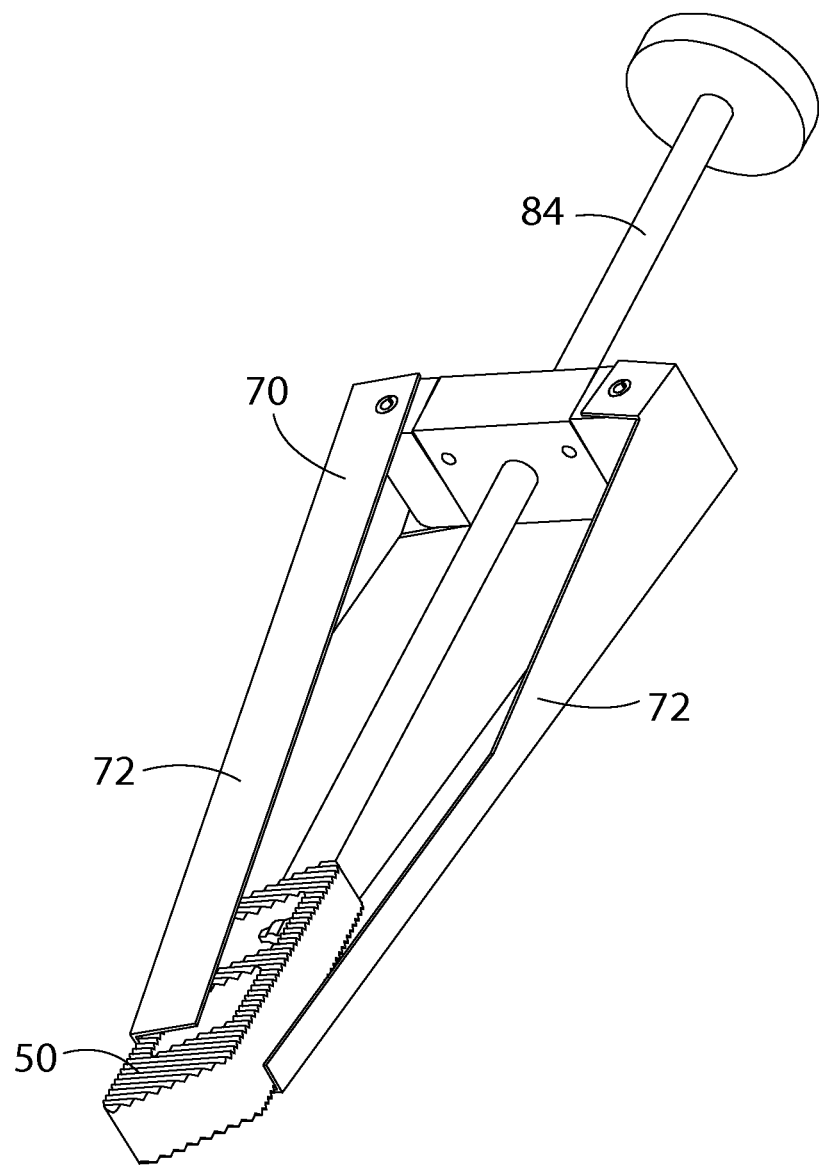
FIG. 21 depicts the shim tool, implant, and impact rod assembly shown in FIG. 20, showing the shim tool in the configuration it is in when the implant passes out of the shim tool during an implantation procedure.
Figure 22:
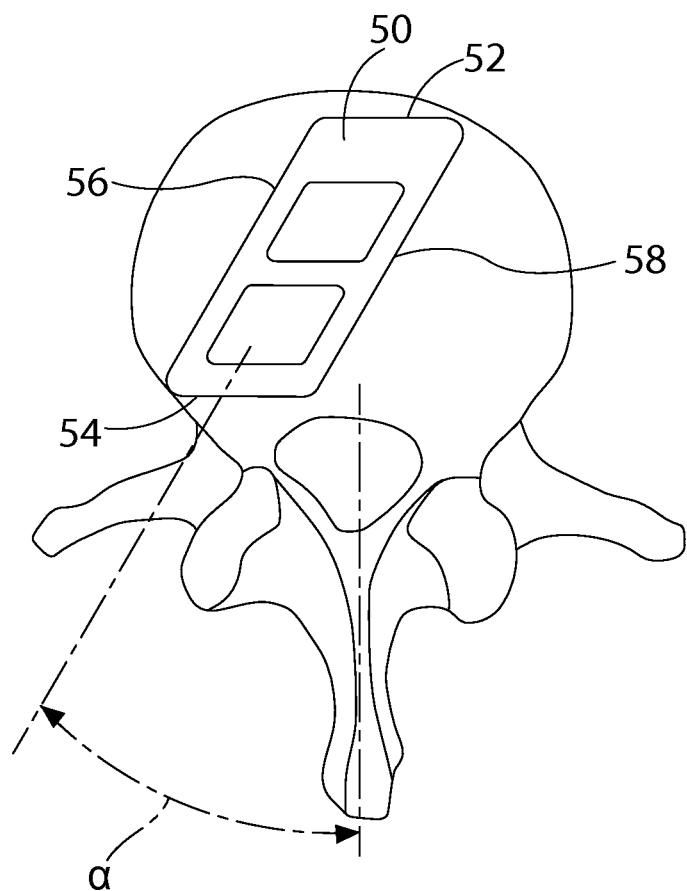
FIG. 22 is similar to FIG. 5 except that it depicts the implant shown in FIGS. 12-18 in a spine at an implantation angle $\alpha$.

In use, a portion of an impact rod 84 is preferably inserted through the impact rod guide hole 82 of the shim tool assembly 70 and is attached to an implant 50 as shown in FIGS. 20 and 21. As shown in FIG. 20, the shims 72 of the shim tool assembly 70 are then pivoted toward each other in a manner such that L-shaped distal ends 74 of the shims together define a small rectangular passageway approximate 10 mm by 5 mm in size. This allows the shims 72 to be inserted between two vertebrae through Kambin's triangle with minimal risk of damaging the adjacent nerve root or the thecal sac. After inserting the shims 72 through Kambin's triangle, the implant 50 can then be urged toward the distal ends 74 of the shims along the passageway that is bounded by the shims. At some point as the implant is urged toward the distal ends of the shims, the implant 50 will engage the shims 72 and urge the shims apart, eventually to a degree such that the implant can pass out of the rectangular passageway defined by the shims. Thus the shims 72 spread apart only after they are in position between vertebrae and only to the degree necessary to allow for the passage of the implant 50. After the implant 50 is in its proper position between the vertebrae, as is shown in FIG. 22, the impact rod 84 and the shims 72 are simply removed from the patient.

Although the preferred method of implanting an implant in accordance with the invention is to guide the implant through Kambin's triangle, it should be appreciated that the implant need not be passed through Kambin's triangle to be implanted. Preferably however, the implant is guided into position between two vertebrae lateral to the dura/thecal sac of the spine and medial to an adjacent exiting nerve root.

In view of the foregoing, it should be appreciated that the invention has several advantages over the prior art.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

It should also be understood that when introducing elements of the present invention in the claims or in the above description of exemplary embodiments of the invention, the terms "comprising," "including," and "having" are intended to be open-ended and mean that there may be additional elements other than the listed elements. Additionally, the term "portion" should be construed as meaning some or all of the item or element that it qualifies. Moreover, use of identifiers such as first, second, and third should not be construed in a manner imposing any relative position or time sequence between limitations. Still further, the order in which the steps of any method claim that follows are presented should not be construed in a manner limiting the order in which such steps must be performed.

What is claimed is:

1. A method of implanting a spinal interbody fusion implant between two vertebrae of a spine, the method comprising inserting the implant into a patient through a posterior incision and guiding the implant into a position between the two vertebrae using a pair of shims, the implant being between the shims and the shims being between the vertebrae as the implant is guided into place, the pair of shims being connected to each other via a connector member, each of the shims having a proximal longitudinal end that is pivotally connected to the connector member about two mutually perpendicular axes and is pivotally fixed relative to the connector member about a third mutually perpendicular axis, each of the shims having a distal longitudinal end that has an L-shaped transverse cross-section, the step of guiding the implant into a position between the two vertebrae comprising:

initially positioning the distal longitudinal ends of the shims in a manner such that the L-shaped transverse cross-sections are positioned between the two vertebrae and together define a small rectangular passageway that is too small for the implant to pass through;

and thereafter spreading the distal longitudinal ends of the shims horizontally and vertically apart from each other in a manner such that the L-shaped transverse cross-sections together define a larger rectangular passageway through which the implant can pass.

2. A method in accordance with claim 1 wherein the spreading of the distal longitudinal ends of the shims is performed by urging the implant toward the distal ends of the shims along a path that lies between the shims and that extends between the proximal and distal longitudinal ends of the shims.

3. A method in accordance with claim 2 wherein the urging of the implant toward the distal ends of the shims is performed using a impaction rod that at least in part is guided via the connecting member.

4. A method in accordance with claim 1 wherein the implant is guided into the position between the two vertebrae along an implantation vector that intersects the sagittal plane of the spine at an angle of between ten and forty degrees.

5. A method in accordance with claim 4 wherein the implant is guided between the two vertebrae lateral to the dura/thecal sac of the spine and medial to an adjacent exiting nerve root.

6. A method in accordance with claim 4 wherein the implant is generally rhomboidal in shape and comprises a leading end and a trailing end, and the position between the two vertebrae is such that the leading end of the implant intersects the midsagittal plane of the spine and lies generally parallel to the coronal plane of the spine.

* * * * *